United States Patent [19]

Weitzman et al.

[11] Patent Number: 6,096,718
[45] Date of Patent: Aug. 1, 2000

[54] TISSUE SPECIFIC ADENOVIRUS VECTORS FOR BREAST CANCER TREATMENT

[75] Inventors: Sigmund Weitzman, Winnetka; Bayar Thimmapaya, Lake Forest; Leonard Anderson, Chicago, all of Ill.

[73] Assignee: Gene Targeting Corp., Winnetka, Ill.

[21] Appl. No.: 08/872,762

[22] Filed: Jun. 5, 1997

[51] Int. Cl.[7] .......................... A01N 43/04; A01N 61/00; C12N 15/00

[52] U.S. Cl. .................. 514/44; 514/44; 514/1; 435/320.1

[58] Field of Search ............................. 514/44; 424/93.2, 424/93.1; 435/320.1

[56] References Cited

U.S. PATENT DOCUMENTS

| 5,612,185 | 3/1997 | Uhr et al. ................................. 435/7.23 |
| 5,631,236 | 5/1997 | Woo et al. ................................. 514/44 |

FOREIGN PATENT DOCUMENTS

WO 95/05835  3/1995  WIPO .

OTHER PUBLICATIONS

Jolly D., Cancer Gene Therapy, vol. 1 (1), p. 51–64, 1994.
Stinnakre et al., FEBS, vol. 284 (1), p. 19–22, Jun. 1991.
Hall et al., Biochem. J., vol. 242, p. 735–742, 1987.
Shani et al., Transgenic Research, vol. 1, p. 195–208, 1992.
Alam, J., et al.(1990) "Reporter Genes: Application to the Study of Mammalian Gene Transcription," *Anal. Biochem.*, 188:245–254.
Ali, S., et al., (1990) "Characterisation of the Alleles Encoding Ovine β–Lctoglobulins A and B," *Gene*, 91:201–207.
Alvarez, R., et al., (1997) "A Phase I Study of Recombinant Adenovirus Vector–Mediated Intraperitoneal Delivery of Herpes Simplex Virus Thymidine Kinase (HSV–TK) Gene and Intravenous Ganciclovir for Previously Treated Ovarian and Extraovarian Cancer Patients," *Human Gene Therapy*, 8:597–613.
Chen, L., et al., (1995) "Breast Cancer Selective Gene Expression and Therapy Mediated by Recombinant Adenoviruses Containing the DF3/MUC1 Promoter," *J. Clin. Invest.*, 96:2775–2782.
Chen, S.H., et al., (1996) "Combination Suicide and Cytokine Gene Therapy for Hepatic Metastases of Colon Carcinoma: Sustained Antitumor Immunity Prolongs Animal Survival," *Cancer Research*, 56:3758–3762.
Gould, M.N., (1995) "Rodent Models for the Study of Etiology, Prevention and Treatment of Breast Cancer," *Cancer Biology*, 6:147–152.
Graham, F.L., et al., (1977) "Characteristics of a Human Cell Line Transformed by DNA from Human Adenovirus Type 5," *J. Gen. Virol.*, 36:59–72.
Halbert, D.N., et al., (1985) "Adenovirus Early Region 4 Encodes Functions Required for Efficient DNA Replication, Late Gene Expression, and Host Cell Shutoff," *J. Virol.*, 56:250–257.

Hall, L., et al., (1987) "Organization and Sequence of the Human α–Lactalbumin Gene," *Biochem J.*, 242:735–742.
Harris, S., et al., (1991) "Developmental Regulation of the Sheep β–Lactogloblin Gene in the Mammary Gland of Transgenic Mice," *Dev. Genet.*, 12:299–307.
Jones, N., et al., (1979) "Isolation of Adenovirus Type 5 Host Range Deletion Mutants Defective for Transformation of Rat Embryo Cells," *Cell*, 17:683–689.
Kanai, F., et al., (1997) "In Vivo Gene Therapy for α–Fetoprotein–Producing Hepatocellular Carcinoma by Adenovirus–Mediated Transfer of Cytosine Deaminase Gene[1]," *Cancer Research*, 57:461–465.
Katayose, D., et al., (1995) "Cytotoxic Effects of Adenovirus–Mediated Wild–Type p53 Protein Expression in Normal and Tumor Mammary Epithelial Cells," *Clin. Canc. Res.*, 1:889–897.
Kwong, Y.L., et al., (1996) "Adenoviral–Mediated Suicide Gene Therapy for Hepatic Metastases of Breast Cancer," *Cancer Gene Therapy*, 3(5):339–344.
Leimeg, T., et al., (1996) "High–Efficiency Transduction of Freshly Isolated Human Tumor Cells Using Adenoviral Interleukin–2 Vectors," *Human Gene Therapy*, 7:1233–1239.
Manome, Y., et al., (1994) "Enhancer Sequences of the DF3 Gene Regulate Expression of the Herpes Simplex Virus Thymidine Kinase Gene and Confer Sensitivity of Human Breast Cancer Cells to Ganciclovir," *Cancer Res.*, 54:5408–5413.
Marcel, T., et al., (1997) "The TMC Worldwide Gene Therapy Enrollment Report, End 1996," *Human Gene Therapy*, 8:775–800.
Marini III, F.C., et al., (1995) "Assessment of Bystander Effect Potency Produced by Intratumoral Implantation of HSVtk–Expressing Cells Using Surrogate Marker Secretion to Monitor Tumor Growth Kinetics," *Gene Therapy*, 2:655–659.
Ohwada, A., et al., (1996) "Regional Delivery of an Adenovirus Vector Containing the *Escherichia coli* Cytosine Deaminase Gene to Provide Local Activation of 5–Fluorocytosine to Suppress the Growth of Colon Carcinoma Metastatic to Liver," *Human Gene Therapy*, 7:1567–1576.
Ranheim, S., et al., (1993) "Characterization of Mutants within the Gene for the Adenovirus E3 14.7–Kilodalton Protein Which Prevents Cytolysis by Tumor Necrosis Factor," *Journal of Virology*, 67(4):2159–2167.

(List continued on next page.)

*Primary Examiner*—Bruce R. Campell
*Assistant Examiner*—Shin-Lin Chen
*Attorney, Agent, or Firm*—Barnes & Thornburg; Alice O. Martin

[57] ABSTRACT

Replication defective adenoviral vectors serve as vehicles for genes encoding products that kill cells in which the genes are transferred and activated. The novel vectors include tissue specific promoters, and are successful in targeting mammalian cancer cells, in particular human breast cancer cells, and causing tumors to regress.

1 Claim, 5 Drawing Sheets

OTHER PUBLICATIONS

Saito, I., et al., (1985) "Construction of Nondefective Adenovirus Type 5 Bearing a 2.8–Kilobase Hepatitos B Virus DNA Near the Right End of Its Genome," *Journal of Virology*, 54(3):711–719.

Swaminathan, S., et al., (1996) "Transactivation of Adenovirus E2–early Promoter by E1A and E4 6/7 in the Context of Viral Chromosome," *J. Mol. Biol.*, 258:736–746.

Yee, D., et al., (1996) "Adenovirus–Mediated Gene Transfer of Herpes Simplex Virus Thymidine Kinase in an Ascites Model of Human Breast Cancer," *Human Gene Therapy*, 7:1251–1257.

Jolly D. (Cancer Gene Therapy, vol. 1, No. 1, 1994, p51–64).

Stinnakre et al. FEBS (Fed Eur Biochem Soc) LETT 284 (1). 1991. 19–22).

Myal et al. (Mol Cell Endocrinol 80 (1–3). 1991. 165–176).

Mastrangelo et al. (Seminars in Oncology, vol. 23, 1996, p4–21).

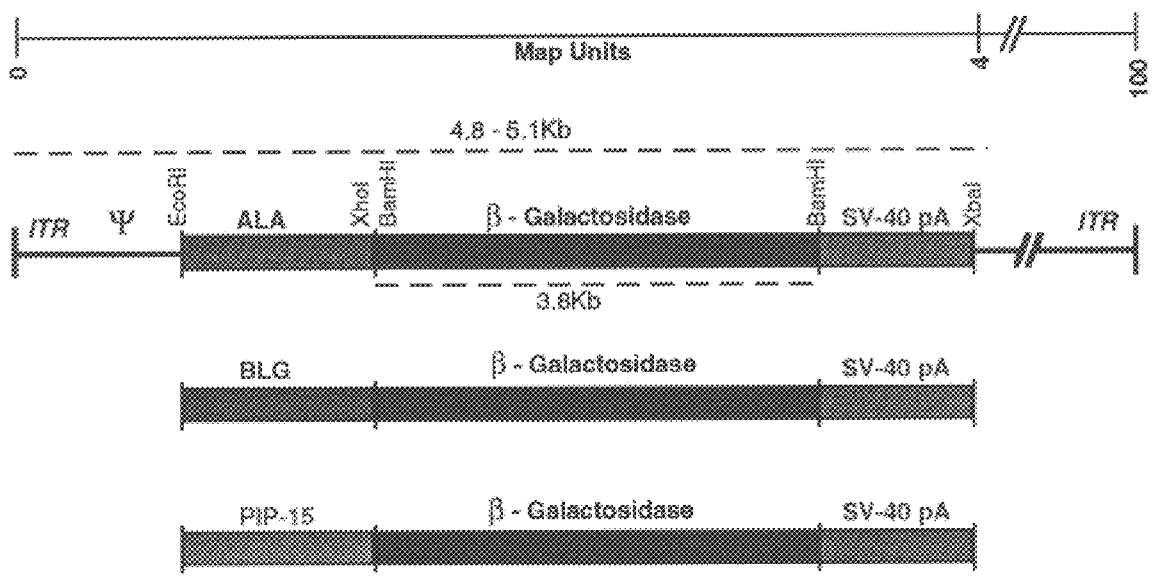
Figure 1. Reporter Vectors

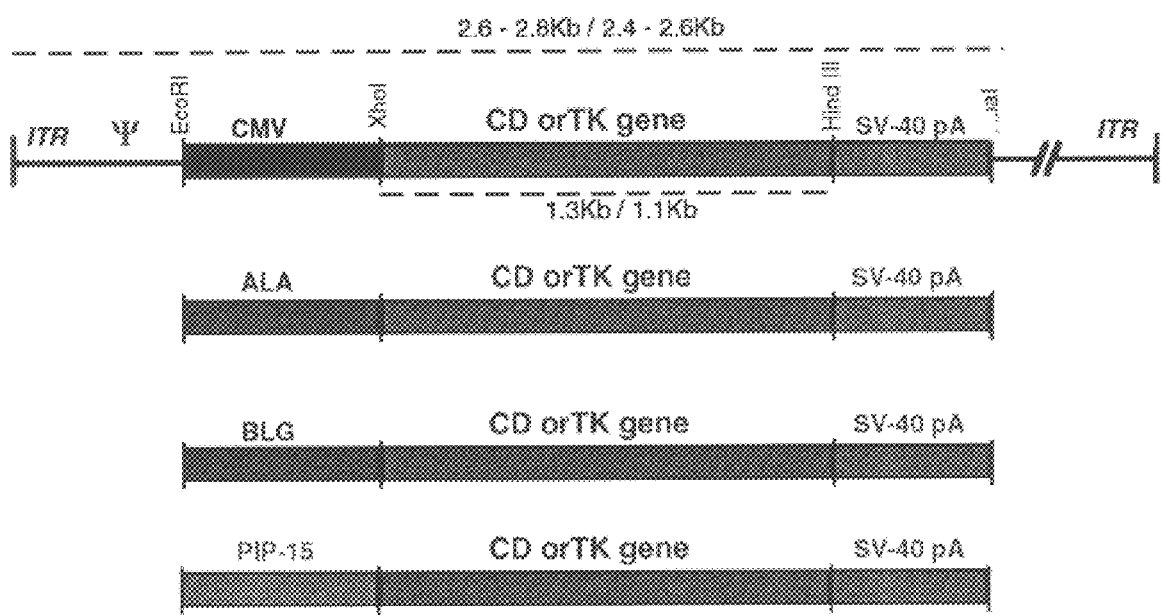
Figure 2. Therapeutic Vectors

E1a Fragment →

TISSUE SPECIFIC ADENOVIRUS VECTORS FOR BREAST CANCER TREATMENT

The U.S. government may have rights in this invention pursuant to NIH1P20CA65764-01.

Tissue specific adenovirus vectors target breast cancer cells with genes that encode products that kill the cells.

Despite important advances in early detection and treatment, breast cancer remains a major cause of death, with more than 40,000 deaths expected in the U.S. alone in 1996. Even with modern chemotherapy and hormone therapy, metastatic breast cancer remains virtually incurable. Thus, it is clear that novel approaches to therapy are needed.

Cancer therapies using recombinant genetic systems have been proposed. Recombinant systems using viral genomes offer the possibility of transferring genes to cancer cells that will deleteriously affect the cells. Consequently, viral genomes have been proposed as the foundation for the construction of vectors designed for specific purposes. The adenovirus is an example of such a genome. One advantage of adenovirus vectors is the absence of risk of insertional mutagenesis that is associated with retroviral vectors. However the difficulties in growing adenovirus, in particular adenovirus that have certain genetic alterations, and undesirable immunological response of the hosts to the vectors, have limited the availability of the virus for recombinant genetic applications.

The adenoviral genome is approximately 36000 base-pairs (bp) in length. The genome of most viruses is traditionally divided into 100 map units in which 1 map unit represents 1/100th of the entire viral genome. Therefore, for adenoviruses, 1 map unit represents 360 bp. Several genes play key roles in an adenoviral infection. One set of these genes, termed "early genes," in the "E1" region which is from 1–4 map units in length, are immediately expressed upon infection of a host cell. Proteins expressed from the E1 region of adenovirus are needed to activate other genes in the viral genome and to establish a replicative program for the virus. If the adenovirus is to be used as a vector to transform a host cell with foreign genes without producing virus, it is essential that the E1 region be deleted in recombinant adenoviruses to render them replication-defective.

For some applications, there may be a need to delete the E1 region, yet still preserve the replication capabilities of the adenovirus. For this purpose, the human embryonic kidney cell line 293 is suitable because E1 deleted adenoviruses will replicate in this cell line. This is because the host cells of 293 have been stably transfected with a DNA fragment containing the E1 and pIX genes, consequently are able to express proteins in a constitutive manner. Embryonic kidney cell line 293 provides proteins needed for viral replication after transfection of an E1 deleted adenoviral DNA, and allows the growing adenoviruses to enter a replicative program.

There are reports that another early protein, the E3 region (including about 79–84 map units) of the adenovirus genome can be deleted without affecting the viral yield; that is, E3 is not essential for replication (Leimig et al., 1996; Ranheim et al., 1993; Saito et al., 1985). Viral genomes that have been modified with deletions in both E1 and E3 are able to incorporate approximately 7.5 kilobases (7.5 kb) of exogenous DNA to replace the deleted adenoviral genes.

A variety of gene therapy vectors use suicide genes (Kanai et al., 1997; Kwong et al., 1996; Chen et al., 1996a,b). Recombinant adenoviruses containing the DF3/MUC1 promoter have been reported to effect selective gene expression of β-galactosidase and the herpes simplex virus thymidine kinase gene in DF3 positive breast carcinoma cell lines, in nude mice, and in introperitoneal breast cancer metastases model. (Manome et al., 1994) The approach of Manome et al. was to use genes selectively expressed in tumor cells in recombinant vectors. Herpes simplex virus thymidine kinase (HSV-tk) was transferred to breast cancer cells with a DF3 enhancer/promoter. However, the authors pointed out limitations in clinical applications of the approach due to lack of target cell specificity. The need for "promoters that are not activated in hepatocytes" was cited. This was also a problem related by Yee et al. 1996.

Manome's publication addresses the problem of selective expression in an optimal situation where MCF7 cells have been stably transduced with a retroviral vector containing the DF3 promoter/tk expression cassette. However, there are major flaws in this type of treatment approach. The DF3 (mucin 1) gene, although overexpressed in many breast cancers, is also expressed in other tissues, some of which are vital organs. Moreover, Manome stated that another major obstacle in their treatment approach was the nonspecific nature of gene transduction currently available and concluded that a need for tissue-selective expression vectors exists.

HSV-tk is an example of a cytotoxic or "suicide gene" that can induce cell death in expressing cells. An attractive feature of this particular suicide gene derives from the demonstration that tk-transfected glioma cells can sensitize wild-type glioma cells to Gancyclovir (GCV). This is referred to as an (I)nnocent (B)ystander (E)ffect, which denotes cell killing of non-infected cells that are in close proximity to infected cells. Although the mechanism responsible for this phenomenon has not been clearly elucidated, it is most likely secondary to the passive transfer of the active phosphorylated nucleotide analogue (a "prodrug") from tk-containing cells to tk-naive cells via cell-to-cell connections (i.e., gap junctions). These non-infected (innocent) cells are subsequently killed by the prodrug. Whatever the mechanism, the implication of the IBE for gene therapy is that it may be possible to eradicate a given tumor mass without infecting every cell with the tk-expressing vector.

As another example of adenovirus mediated transfer of a gene, a tumor suppressor p53 protein transfer resulted in cytotoxic effects on normal and tumor cells of lung and mammary epithelial origin (Katayose et al., 1995).

Choice of a promoter for use in recombinant vectors for gene therapy is important. Tissue specific promoters are known in some plants and animals but have not generally been used in clinical applications. This may be due to uncertainty whether heterologuous tissue specific promoters would work in human tissues, whether immunogenic responses would negate the use of the promoter, and how specific promoters would behave in foreign host organisms. Tissue specific promoters include the β-lactoglobulin gene. (Harris et al., 1991).

Further improvements in gene therapy would hasten the successful clinical applications of these new technologies.

SUMMARY OF THE INVENTION

The present invention utilizes a more realistic and effective treatment strategy than available in the art. In the present invention, a therapeutic gene is under the control of a tissue-specific promoter. None of the promoters used are expressed in vital organs, and expression in normal non-lactating breast tissue is virtually undetectable. This provides more treatment options than previously available, and more effective options. Vectors of the present invention are delivered locally or in a systemic manner without the concern of adversely affecting vital organs.

Replication defective adenoviral vectors are constructed carrying "suicide" genes (genes which can kill the cell in which they reside if the genes are activated). These vectors are constructed such that the suicide genes are not active in any vital organs and are expressed in a tissue-specific manner in breast cancer. The tissue specificity is accomplished by cloning specific gene promoters into the vectors. These promoters are cloned from genes which are expressed almost exclusively in breast tissue and breast cancer tissue. Therefore, the expression of genes driven by these promoters is essentially tissue specific. Tissue specificity is demonstrated in tissue culture and in mice. Adenovirus vectors are also deleted in both the E1 and E3 regions to maximize the foreign DNA cloning capacity in this type of vector. The vectors of the present invention facilitate gene therapy of breast cancer by targeting breast cancer cells and killing them.

When the adenovirus vectors of the present invention were used in a mammalian cancer model, surprisingly, there were no traces of the viral vector in other than the target organ, e.g. not in the liver. Also surprising was the strength of the expression in the host as measured by tumor regression.

The recombinant vectors of the present invention are more effective when used in conjunction with prodrugs.

BRIEF DESCRIPTION OF THE DRAWINGS

FIG. 1 presents maps of reporter vectors.

FIG. 2 presents maps of therapeutic vectors.

DESCRIPTION OF THE PREFERRED EMBODIMENT

Figure 3A:
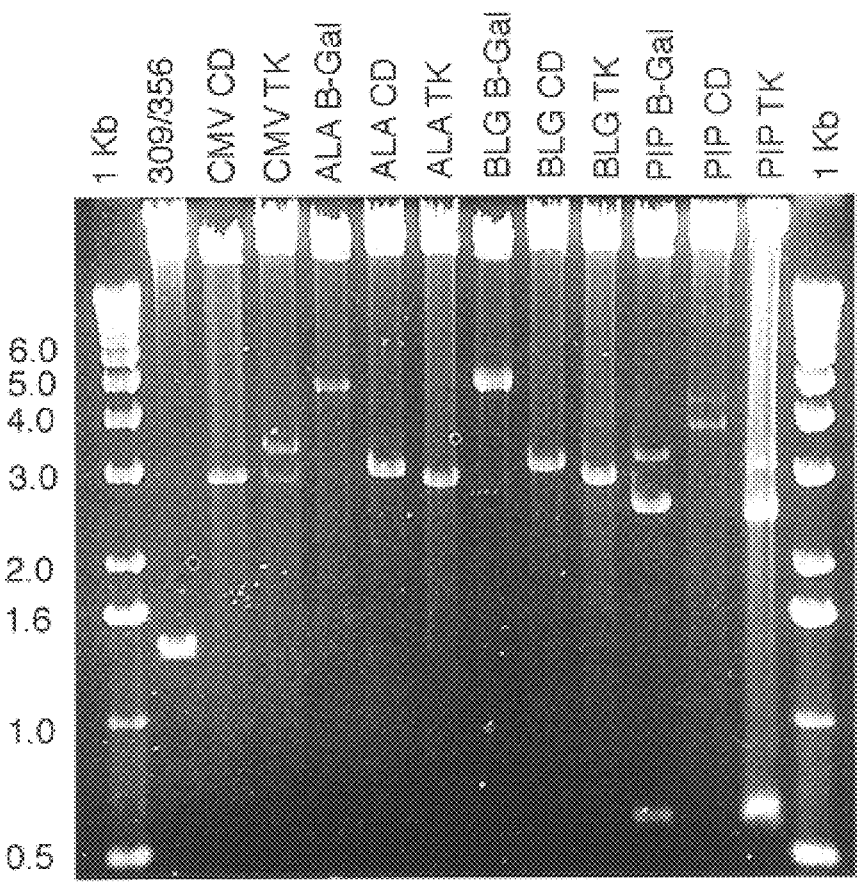
FIG. 3(a) presents the predicted digestion pattern of recombinant viral genomic DNA digested with Xba I; specifically, the FIG. shows purified adenoviral genomic DNA which has been subjected to restriction digestion by XbaI; the digested DNA is then separated by agarose gel (0.6%) electrophoresis; the fragments located below the 6.0 kb marker fragment in each lane depict the expression cassette (promoter, gene, polyA) of the respective adenoviral vector (see top of lanes); lane 2 contains wild type viral DNA and is used as a control.

Tissue specific adenovirus vectors target breast cancer cells with genes that encode products that kill the cells.

1. Tissue Specific Vectors that Target Cancer Cells

Viral vectors are deleted in both the E1 and E3 regions to maximize the foreign DNA cloning capacity in this type of vector. These vectors facilitate gene therapy of breast cancer.

One aspect of the vectors of the present invention that makes them unique is the use of the following tissue specific promoters to drive suicide genes: the α-lactalbumin promoter, (human), (Harris et al., 1991) the β-lactoglobulin promoter (ovine) (Ali et al., 1990), and the prolactin-inducible protein-15 (PIP-15) promoter (human). Vectors using each of these promoters separately in combination with suicide genes such as the herpes virus thymidine kinase gene or the cytosine deaminase gene are aspects of the present invention. For purposes of comparison, the CMV promoter/enhancer is used. This is a strong constitutive promoter, directing genes it controls to synthesize abundant quantities of proteins. Six virus vectors are aspects of the present invention. The activity of 3 thymidine kinase expressing vectors (ALA.tk, BLG.tk, and CMV.tk) were confirmed. The cytosine deaminase vectors were constructed.

A variety of routes for delivery of the vector to the target mammalian tissue includes intravenous injection for systemic therapy of metastatic cancer; intracavitary, intra-arterial, and intralesional routes.

The herpes virus thymidine kinase gene kills cells when it is expressed in the presence of the drug gancyclovir, and the cytosine deaminase gene kills cells when it is expressed in the presence of 5-Fluorocytosine. Therefore, an aspect of the invention is to administer an effective dose of these drugs in conjunction with the vectors. Both Gancyclovir and 5-Fluorocytosine are drugs already approved for humans and are in clinical trials involving gene therapy (Marcel et al., 1997; Alvarez et al., 1997) The clinical regimen for prospective patients includes delivery of the adenoviral vector (tk or cd) by various routes (i.e. intravenous, intratumoral). The specific viral concentrations will have to be determined during the course of therapy. The prodrug (GCV or 5-FC) will then be administered systemically at concentrations that are being used and will be established in current clinical trials.

2. Origin of Adenovirus

The origins of adenoviruses suitable for the invention are described in Swaminathan and Thimmapaya (1996). In an embodiment, the recombinant adenovirus Ad5(309/356) contains specific deletions in the early region 1 (E1), and early region 3 (E3). It is important to use a control virus with this genetic background (that is, including the same mutations) because a different viral genome could introduce unwanted variables that make results of tests difficult to interpret. For example, a recombinant adenovirus with a deletion in the early region 2 (E2) gene is non-viable.

3. Production of Expression Cassettes

Expression cassettes were initially constructed in a pUC18 derived plasmid backbone flanked by NheI and XbaI restriction enzyme sites. These cassettes contained the following sequences; adenoviral inverted terminal repeat and packaging sequences (Ad5 bp 1-375), promoter (CMV, ALA, BLG, PIP-15) and gene (β-galactosidase, HSV-thymidine kinase, cytosine deaminase) sequences followed by SV-40 polyadenylation sequences. The promoters were isolated from human genomic DNA using the polymerase chain reaction (PCR). The genes were isolated or subcloned from other plasmid constructs. The β-galactosidase gene was amplified via PCR from the plasmid pNassβ (Clontech). The HSV-tk gene (bp 301-1448) was amplified from the plasmid pMC1-tk (Marini et al. 1995). The plasmid used in the construction of the cytosine deaminase (CD) viruses was obtained from Dr. Ronald Crystal (Ohwada et al., 1996). The SV-40 polyadenylation sequences were subcloned from the plasmid pNASSβ via NotI and HindIII restriction sites (Alam, 1990). Promoter sequences were isolated from MCF-10a cells (ATCC# CRL 10317).

The expression cassettes were released from the plasmid background via digestion with NheI and XbaI restriction enzymes and ligated to an XbaI digested adenoviral genomic DNA fragment (Ad 309/356) containing sequences from 4–100 map units. The ligation mixture was then transfected into subconfluent (75%) cell line 293 cells via the calcium phosphate co-precipitation method. These cells were then harvested in growth media (DMEM+2% DCS) after showing evidence of 80% cytopathic effect (CPE). The cytopathic effect (CPE) is defined as a dramatic change in morphology and detachment from the growing surface (i.e. tissue culture plate) subsequent to viral infection. After harvesting, the cells were then subjected to 3 cycles of rapid freeze/thawing. The cellular debris was cleared by centrifugation at 2500 rpm for 10 min. and the lysate containing the recombinant adenovirus was stored at −20° C. for future use.

FIG. 1 shows maps of reporter vectors with the β-galactosidase gene; FIG. 2 shows maps of therapeutic vectors with suicide genes.

4. Isolation of a Viral Clone

Plaque assays were performed on the cell lysates in order to isolate an individual viral clone. The adenoviral containing lysates were serially diluted in DMEM containing 2% DCS and added to subconfluent (80%) cell line 293 (Ad 5 transformed human kidney cells, Graham et al., 1977) cells in 60 mm plates. After 1 hr. of incubation at 37° C., the medium was removed and replaced by F-15 minimal essential medium (MEM) containing 0.85% agar, 0.1% pen/strep, and 4% fetal calf serum (FCS). Single plaques indicative of a single viral infection were isolated and used to reinfect another plate of 293 cells for plaque isolation. After 3 rounds of plaque assays individual plaques were amplified in 293 cells in 10 cm plates for DNA analysis.

5. DNA Analysis

For viral DNA analysis the cell line 293 cell lysates containing virus from plaque infections were harvested. The supernatants were layered onto CsCl cushions, 2.5 ml of heavy (1.45 g/cm$^3$ CsCl/10 mM tris pH 8.0, 1 mM EDTA; refractive index (RI), 1.375) and 2.5 ml of light (1.20 g/cm$^3$ CsCl/10 mM Tris pH8.0, 1 mM EDTA; RI 1.356) and centrifuged in an SW-41 rotor at 30000 rpm for 90 min. at 15° C. To remove the CsCl, the collected virion bands were mixed with 0.1M Tris-HCl pH 8.0 and dialyzed against Tris/EDTA buffer (Tris pH8.0/1 mM EDTA) for 8–10 hours. The virions were then collected and subjected to deproteinization in a solution containing; 1% SDS, 0.1% 0.5M EDTA pH8.0, 2.5 μg pronase, and incubated at 37° C. for 60 min. The solution was then subjected to 2 rounds of phenol/chloroform extractions and the viral DNA was precipitated in 95% and then 70% ethanol. The DNA was then dried in a speedvac apparatus and resuspended in 40 μl of TE buffer.

Restriction digestions were performed as follows; approximately 2 μl of viral DNA was added to a solution containing the restriction enzyme of interest (XbaI or HindIII at a concentration of 2 units/μg DNA), 0.1 volumes restriction enzyme buffer, and sterile water to 20 μl. These reactions were allowed to incubate for 2 hrs. at 37° C. after which the digestion was loaded on a 0.6% agarose gel and run at 34 volts for approximately 12 hours. The gel was then stained with ethidium bromide (EtBr) and viewed under UV light for analysis.

Figure 3B:
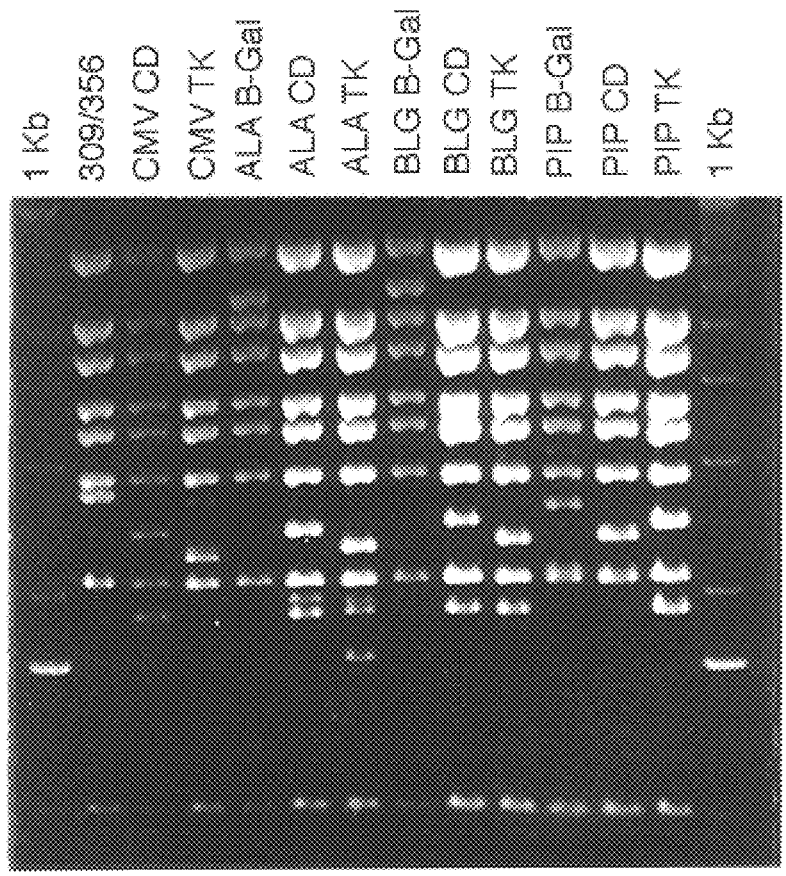
FIG. 3(b) shows purified viral DNA digested with HindIII; the digests were separated by electrophoresis; the arrow denotes a DNA fragment that contains the wild type E1 a gene in lane 2; this fragment is not present in the other lanes which contains genomic DNA from various recombinant adeno-vectors; the Ad 309/356 is a positive control virus which harbors E1 a sequences in a 1.4 kb DNA fragment. This fragment is absent in the other lanes.

FIG. 3A shows the predicted digestion pattern of the recombinant viral vectors. FIG. 3B shows that the DNA fragment containing the E1a gene (arrow) is not present in the recombinant viruses when compared to the control (309/356).

EXAMPLES

The following examples provide illustrations of the present invention, not limitations.

Example 1: Effects of Adenovirus Vectors on Breast Cancer Cell Lines

Figure 4:
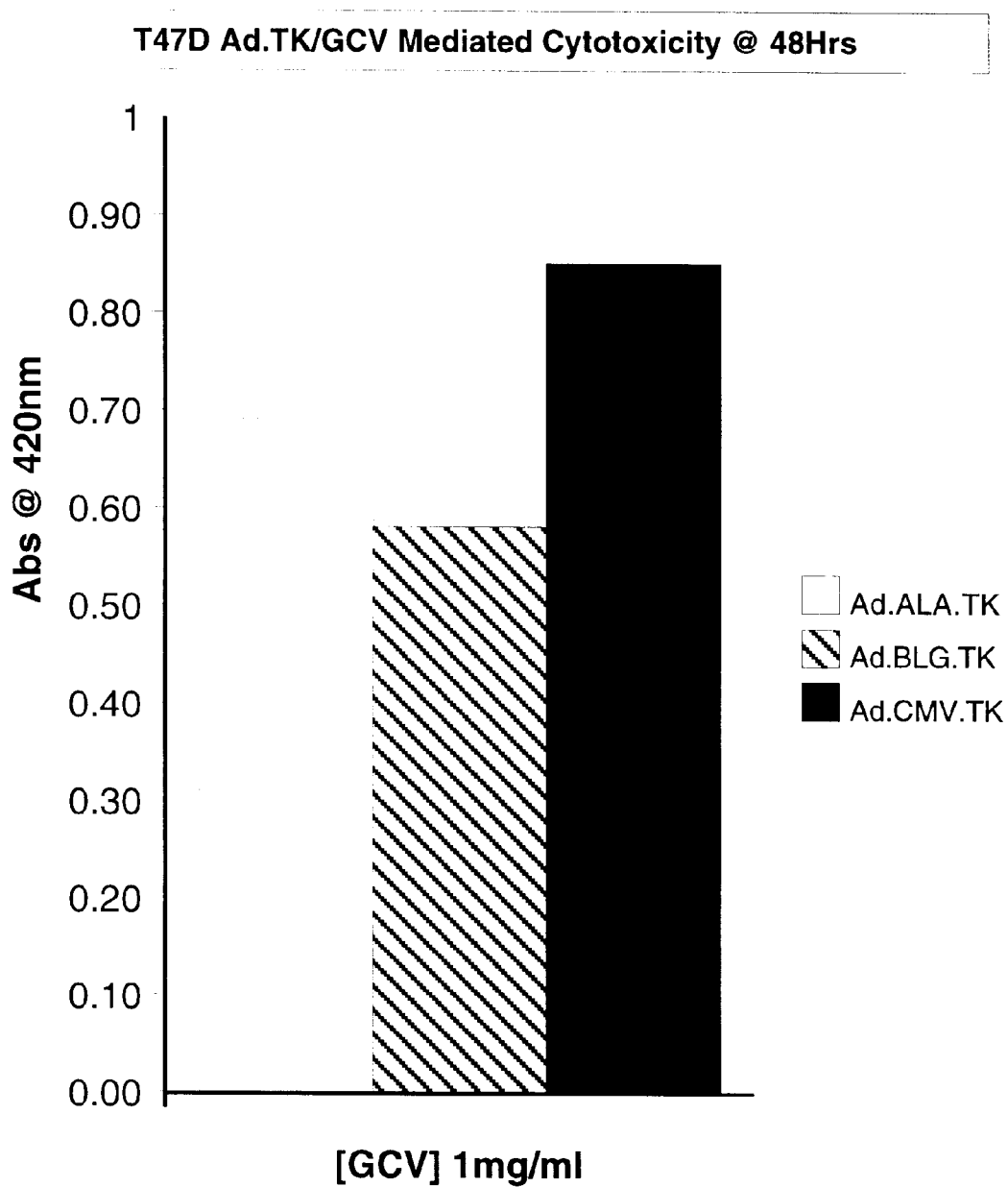
FIG. 4 illustrates LDH release from T47D cells infected with adenovirus vectors of the present invention.

FIG. 4 shows the cell killing effects of the thymidine kinase (TK) viruses in the breast cancer cell line T47D [human breast pleural effusion carcinoma cells (ATCC# HTB 133)] as measured by lactase dehydrogenase (LDH) release from the cells. The y-axis of this graph shows absorbance at 420 nanometers. This is a standard means to measure the cytoxic effects of an exogenous agent added to the cells. The kit for these experiments was obtained from Promega (Cytotox 96) As shown in the graph, a moderate proportion of cells are killed due to conversion of the prodrug gancyclovir (GCV) to the toxic analog by thymidine kinase. This experiment was done using various concentrations of gancyclovir ranging from 0.01 to 10,000 μg/ml media. The highest concentration was toxic to all cells while the lowest showed no toxicity. A concentration of 1 mg/ml, (FIG. 4) in conjunction with the tissue-specific viruses that are an aspect of the invention was the most effective at cell killing.

T47D cells were grown to sub-confluency in RPMI=5% FBS in 60 mm culture dishes. These cells were then infected with recombinant adenoviruses at 5 PFU/cell. One hour post-infection, fresh media with gancyclovir (0.1–10000 μg/ml) was added). LDH release was measured every 24 hours for a total of 48 hours. Each sample is a mean value of triplicate measurements from two experiments. LDH release values obtained from Ad.CMV.B-Gal infections were subtracted from all other infections as shown by the table below.

| Expression Cassette | Absolute Value | Absolute-Control Values |
| --- | --- | --- |
| Ad.CMV.B.-Gal | 1.2 | 0 |
| Ad.ALA.TK | 1.89 | 0.69 |
| Ad.BLG.TK | 1.78 | 0.58 |
| Ad.CMV.TK | 2.05 | 0.85 |

Example 2: Therapeutic Effects of Adenovirus Vectors in Mice

Figure 5:
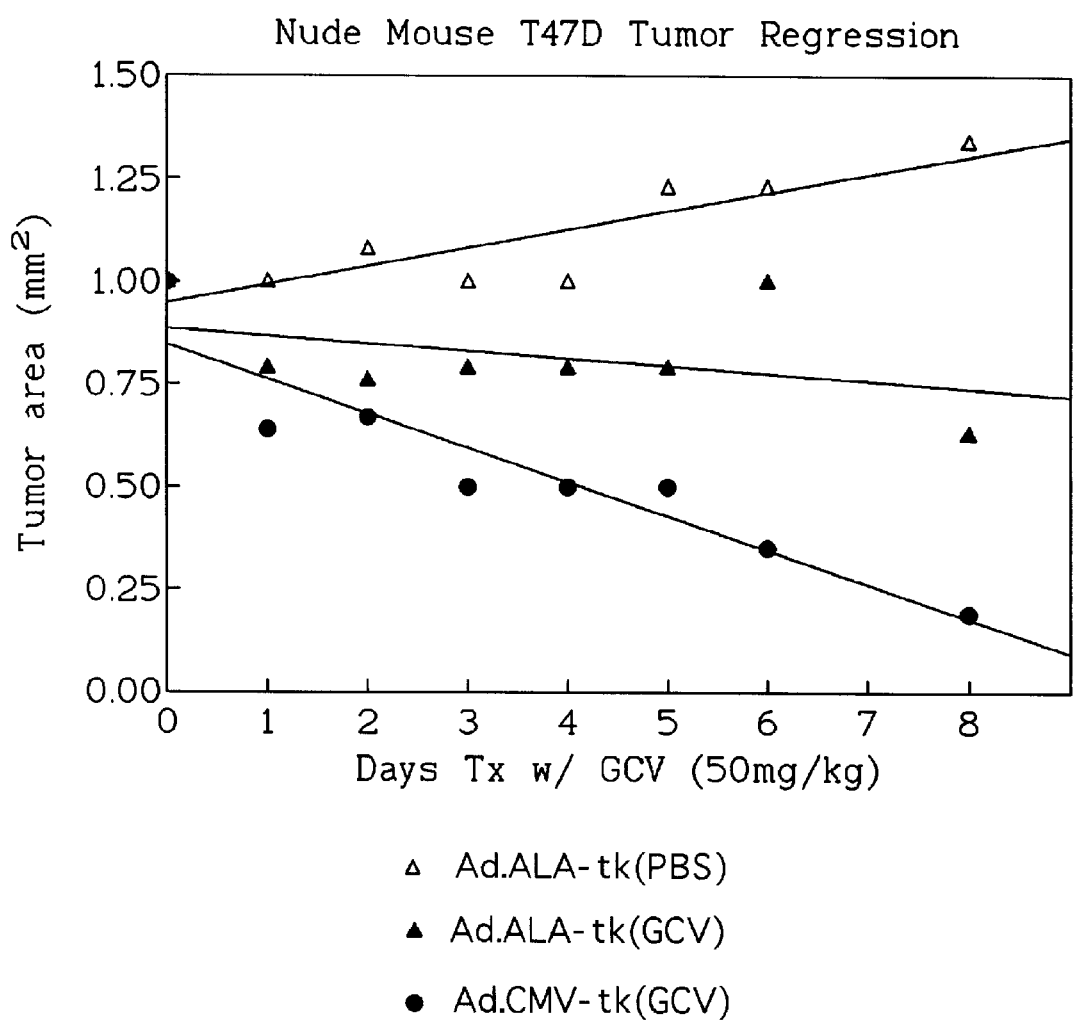
FIG. 5 illustrates tumor regression in nude mice treated with recombinant adenoviral vectors.
Figure 4:
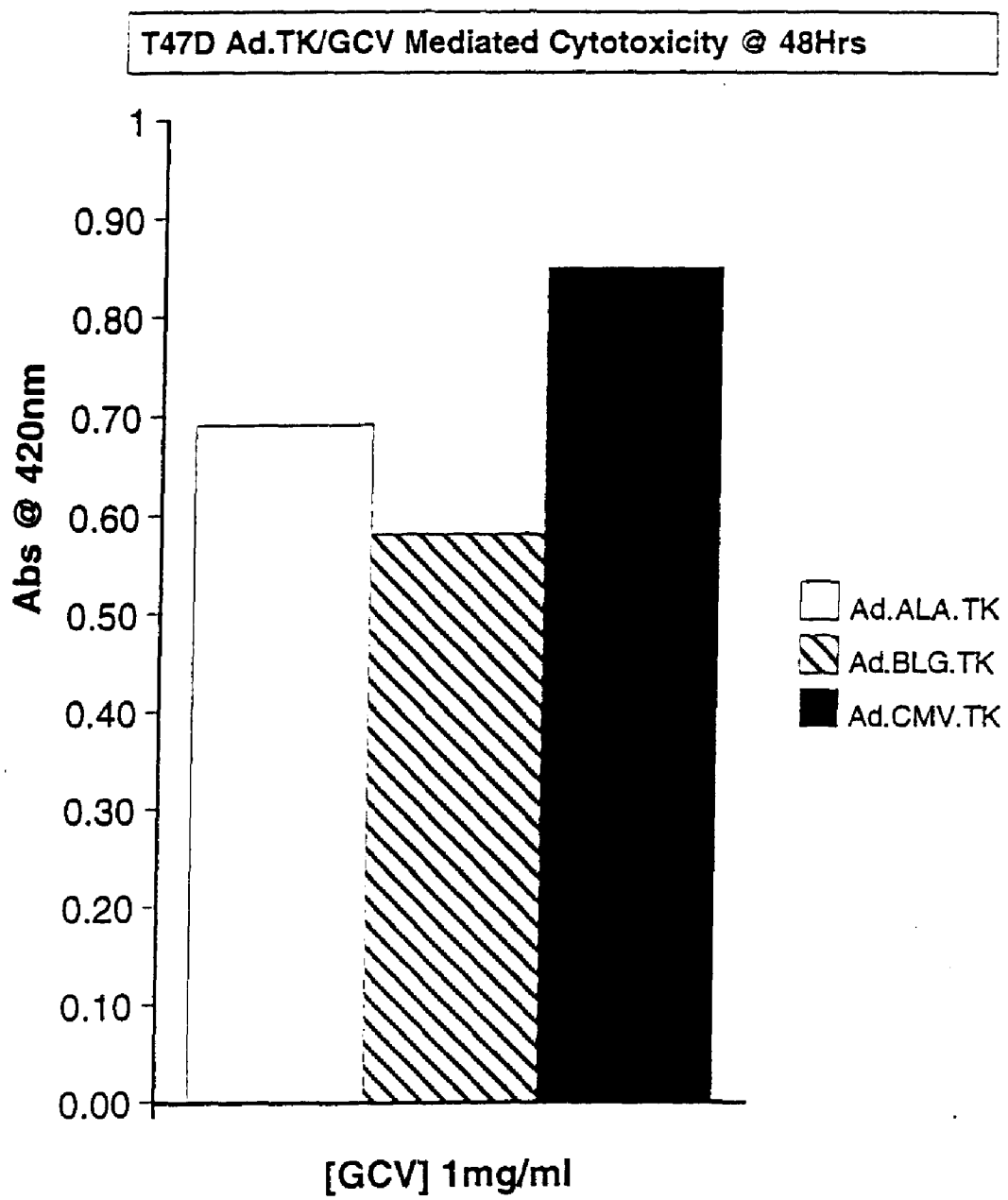

Nude mice are an accepted model for effects of therapies on human cancers (Gould, 1995). FIG. 5 shows the effects of the TK viruses constructed according to the present invention on actual human breast cancer tumors grown in nude mice. T47D cells were injected and allowed to grow as tumors in Balb/c nude mice. TK expressing adenoviruses were injected directly into the tumor and the virus was allowed to express the TK protein for 5 days. Gancyclovir or a suitable vehicle (e.g., PBS) was then injected systemically and the tumor sizes were measured every day for a total period of 8 days. Linear regression analysis of this data shows that the Ad.ALA.TK vector is effective at regressing breast tumors in these mice as compared to Ad.ALA.TK and GCV treated or those treated with vehicle alone or Ad.CM-V.TK treated with GCV. (The CMV promoter has been well characterized and only serves as a positive control in our experiments.)

Nude mice were injected subcutaneously with 10$^7$ T47D cells in the upper flank region and allowed to establish as growing breast tumors. After 2 weeks tumors were injected with 2×10⁸ of recombinant TK expressing adenoviruses. Gancyclovir was administered at a dosage of 50 mg/kg/day via intra-peritoneal (IP) injection for a period of 5 days. Tumor areas were measured using the formula L×W²/2 each day for a total of 8 days. L×W²/2 is a formula used to measure tumor area where L is the length of the tumor in millimeters and W is the width in millimeters. The area, expressed in millimeters squared (mm²), of a given tumor can be calculated when numerical values are substituted for the variables in this formula. This graph shows a linear regression of the calculated tumor sizes. The initial measurement taken at day 0 before GCV treatment was given a value of 1. All subsequent measurements are a percentage of this value. The y-axis of this graph is denoted as follows: All mouse tumors were of various sizes before treatment. To normalize for this variability in tumor size, mouse tumors were given a value of 1.0 regardless of tumor volume. All subsequent measurements are a percentage of the starting value.

FIG. 5 demonstrates the strong expression of the vector as measured by tumor regression. The magnitude of the regression is obvious compared to regression caused by other treatment strategies.

DOCUMENTS CITED

Alam, J. (1990) *Anal. Biochem.* 188:245.

Ali, S. et al. (1990) *Gene.* 91;201–207.

Alvarez, R. et al. (1997) *Human Gene Therapy.* 8(5):597–613.

Chen, L. et al., (1996) *J. Mol. Biol.* 258:736–746.

Chen, S. H. et al. (1996) *Cancer Research.* 56(16):3758–3762.

Gould, M. N. (1995) *Cancer Biology.* 6:147–152.

Graham, F. L. et al. (1977) *J. Gen. Virol.* 36:59–72.

Halbert, D. N. et al. (1985) *J. Virol.* 56:250–257.

Harris, S. et al. (1991) *Dev. Genet.* 12:299–307.

Jones, N. and Shenk, T. (1979) *Cell.* 17:683–689.

Kanai, F. et al. (1997) *Cancer Research.* 57(3):461–465.

Katayose, D. et al. (1995) *Clin. Canc. Res.* 1:889–897.

Kwong, Y. L. et al. (1996) *Cancer Gene Therapy.* 3(5):339–344.

Leimeg, T. et al. (1996) *Human Gene Therapy.* 7(10):1233–1239.

Manome, Y. et al. (1994) *Cancer Res.* 54:5408–5413.

Marcel, T. et al. (1997) *Human Gene Therapy.* 8(6):775–800.

Marini, F. C. et al. (1995) *Gene Therapy* 2(9):655–659.

Ohwada, A. et al. (1996) *Human Gene Therapy.* 7(13):1567–1576.

Ranheim, S. et al. (1993) *Journal of Virology.* 67(4):2159–2167.

Saito, I. et al. (1985) *Journal of Virology.* 54(3):711–719.

Swaminathan, S. and Thimmapaya, B. (1996) *J. Mol. Biol.* 258:736–746.

Yee, D. et al. (1996) *Human Gene therapy.* 7:1251–1257.

What is claimed is:

1. A method for killing breast cancer cells in a tumor in a mammal, comprising:

a. delivering to the tumor a replication incompetent adenovirus vector having deletions in the adenoviral E1 and E3 genes, said adenovirus vector comprising a human α-lactalbumin promoter operatively linked to the HSV-TK gene, whereby the HSV-TK gene is expressed, and b. administering to the mammal an effective amount of a gancyclovir, whereby the breast cancer cells are killed.

* * * * *

UNITED STATES PATENT AND TRADEMARK OFFICE
CERTIFICATE OF CORRECTION

PATENT NO.   : 6,096,718
DATED        : August 1, 2000
INVENTOR(S)  : Sigmund Weitzman and Bayar Thimmapaya It is certified that error appears in the above-identified patent and that said Letters Patent is hereby corrected as shown below:

<u>Drawings,</u>
Fig. 4, sheet 4 of 5, the first bar of the graph has been omitted. Please substitute in lieu thereof the attached formal drawing noted as "Exhibit A".

Signed and Sealed this

Thirty-first Day of December, 2002

JAMES E. ROGAN
*Director of the United States Patent and Trademark Office*